(12) United States Patent
Kim

(10) Patent No.: US 10,744,560 B1
(45) Date of Patent: Aug. 18, 2020

(54) NANOPARTICLE COMPOSITION HAVING ANTIBACTERIAL AND PYROGENIC PROPERTIES AND ITS MANUFACTURING METHOD

(71) Applicant: William Kim, Clifton, NJ (US)

(72) Inventor: William Kim, Clifton, NJ (US)

( * ) Notice: Subject to any disclaimer, the term of this patent is extended or adjusted under 35 U.S.C. 154(b) by 67 days.

(21) Appl. No.: 15/937,207

(22) Filed: Mar. 27, 2018

(51) Int. Cl.
| | |
|---|---|
| *B05D 7/00* | (2006.01) |
| *B32B 5/16* | (2006.01) |
| *B22F 1/00* | (2006.01) |
| *C01B 35/10* | (2006.01) |
| *C08L 23/06* | (2006.01) |
| *C08L 55/02* | (2006.01) |
| *C08L 83/04* | (2006.01) |
| *B82Y 30/00* | (2011.01) |
| *B82Y 5/00* | (2011.01) |

(52) U.S. Cl.
CPC ............ *B22F 1/0062* (2013.01); *C01B 35/10* (2013.01); *C08L 23/06* (2013.01); *C08L 55/02* (2013.01); *C08L 83/04* (2013.01); *B22F 2301/056* (2013.01); *B22F 2302/45* (2013.01); *B22F 2303/01* (2013.01); *B82Y 5/00* (2013.01); *B82Y 30/00* (2013.01)

(58) Field of Classification Search
CPC .............................. C09D 5/14; C09D 167/00
See application file for complete search history.

(56) References Cited

FOREIGN PATENT DOCUMENTS

| CN | 108610817 A | * 10/2018 |
| KR | 100483075 B1 | 5/2005 |
| WO | WO-2014035031 A1 | * 3/2014 |

OTHER PUBLICATIONS

Gedda et al., Antibacterial effect of calcium oxide nano-plates fabricated from shrimp shells, Green Chem., 2015, 17, 3276 (Year: 2015).*
Buasri et al., Calcium Oxide Derived from Waste Shells of Mussel,Cockle, and Scallop as the Heterogeneous Catalyst for Biodiesel Production, The Scientific World Journal, vol. 2013, Article ID 460923, 7 pages http://dx.doi.org/10.1155/2013/460923 (Year: 2013).*

* cited by examiner

*Primary Examiner* — Hoa (Holly) Le
(74) *Attorney, Agent, or Firm* — Michael J. Feigin, Esq.; Feigin and Fridman LLC

(57) ABSTRACT

The present invention relates to a nanoparticle composition having antibacterial and exothermic properties and a manufacturing method thereof, more particularly, a nanoparticle composition with very good antibacterial and exothermic properties obtained by preparing an ionized calcium powder from shells obtained through foreign matter removing, cleaning, drying, sintering, cooling and pulverizing processes, and passing it through a tourmaline mixing stage, a surfactant treatment stage, a synthetic resin mixing stage and a nanoparticle molding stage, and a manufacturing method thereof.

9 Claims, 21 Drawing Sheets

[fig. 1]
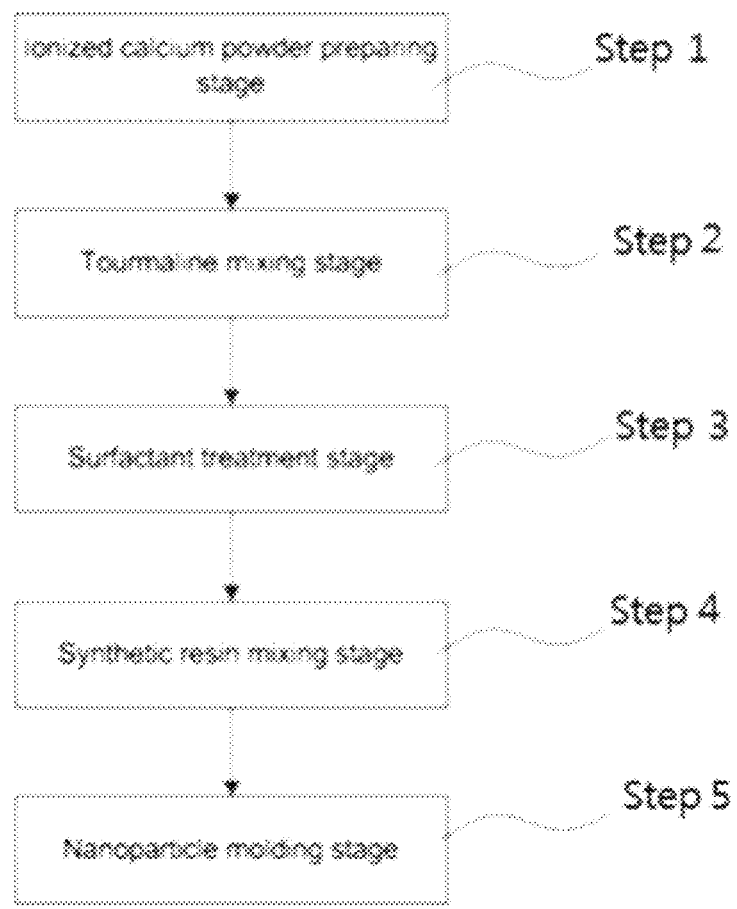

[fig. 2]
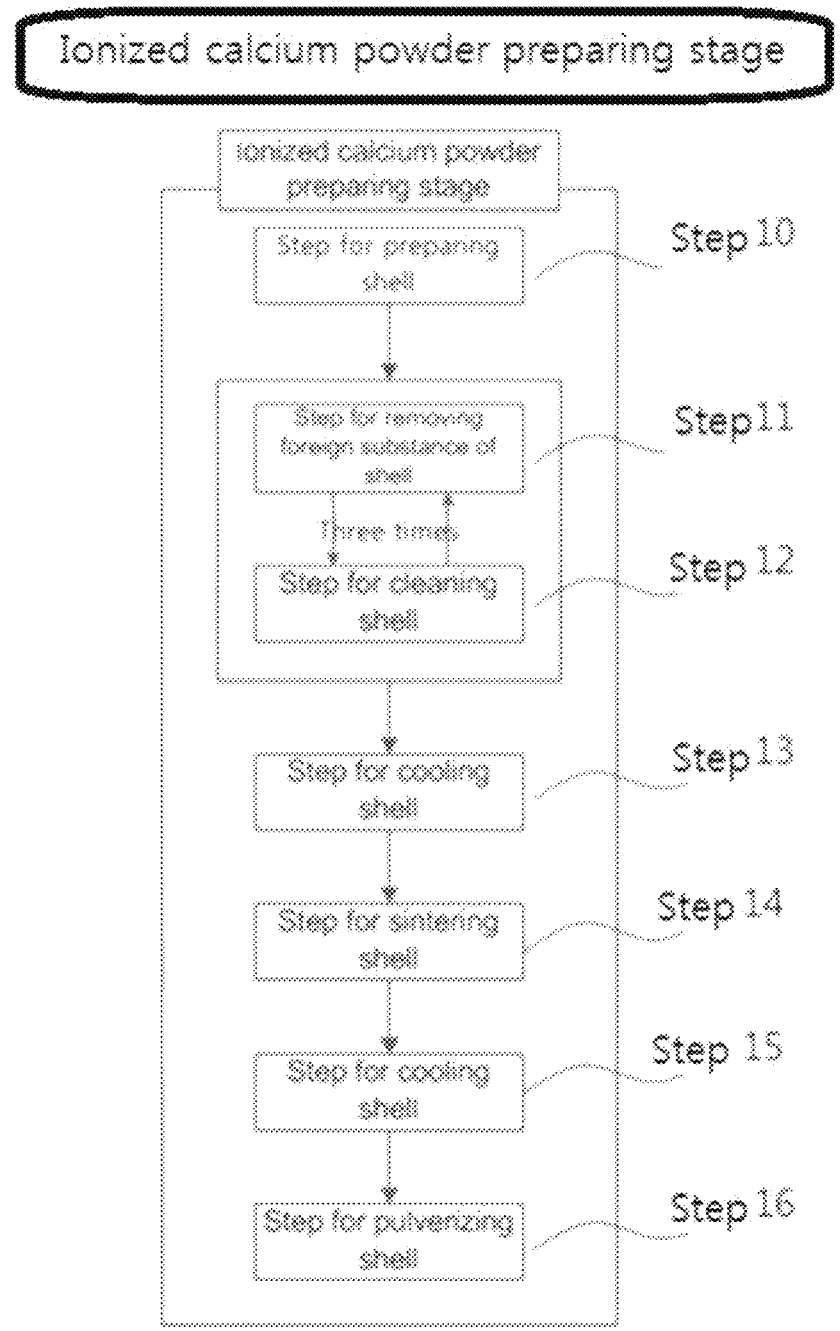

[fig. 3]

[fig.4]

TEST REPORT

Report no.: ES12B19001

Test result

| Test Item | | Test result | | | Test method |
|---|---|---|---|---|---|
| | | Initial concentration (CFU/mL) | Concentration after 24 hours (CFU/mL) | Bacterial reduction rate (%) | |
| Antibacterial test by Escherichia coli | Blank | $3.4 \times 10^5$ | $4.8 \times 10^7$ | - | KCL-FIR-1003 : 2011 |
| | Antibacterial plastic (general-untreated) | $3.4 \times 10^5$ | $4.7 \times 10^7$ | 2.0 | |
| Antibacterial test by Pseudomonas aeruginosa | Blank | $3.6 \times 10^5$ | $5.0 \times 10^7$ | - | |
| | Antibacterial plastic (general-untreated) | $3.6 \times 10^5$ | $4.8 \times 10^7$ | 4.0 | |
| Antibacterial test by Staphylococcus aureus | Blank | $2.9 \times 10^5$ | $4.6 \times 10^7$ | - | |
| | Antibacterial plastic (general-untreated) | $2.9 \times 10^5$ | $4.5 \times 10^7$ | 2.1 | |

* CFU : Colony Forming Unit
* Concentration of bacteria inoculum (CFU/mL) : Escherichia coli : $3.4 \times 10^5$
  Pseudomonas aeruginosa : $3.6 \times 10^5$
  Staphylococcus aureus : $2.9 \times 10^5$

* strain used : *Escherichia coli* ATCC 8739
  *Pseudomonas aeruginosa* ATCC 15442
  *Staphylococcus aureus* ATCC 6538P

* Test group : 5 cm × 5 cm,
  Control group : Stomacher film : 5 cm × 5 cm

*the way to trust* KCL
TEST REPORT
Report no.: ES12B19001
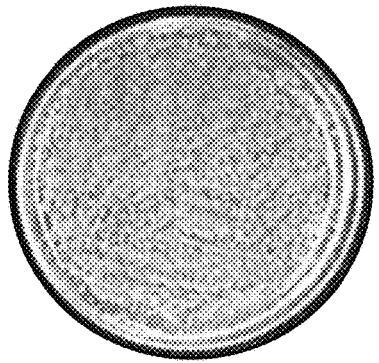
K C L
Antibacterial experiment
Blank (24h)
*Escherichia coli* ATCC 8739
[photo 1]
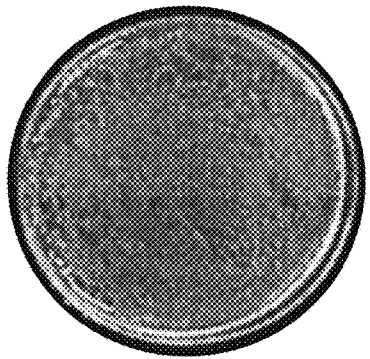
K C L
Antibacterial experiment
Antibacterial plastic
(general-untreated)
*Escherichia coli* ATCC 8739
[photo 2]
FORM OP-20-01-06(0)
FIG. 5

*the way to trust* KCL
TEST REPORT
Report no.: ES12B19001
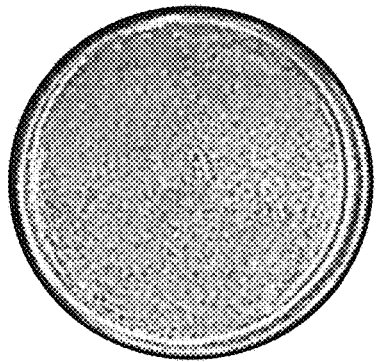
K C L
Antibacterial experiment
Blank (24h)
*Pseudomonas aeruginosa*
ATCC 15442
[photo 3]
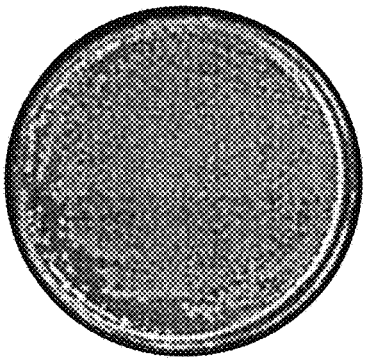
K C L
Antibacterial experiment
Antibacterial plastic
(general-untreated)
*Pseudomonas aeruginosa*
ATCC 15442
[photo 4]
4 of total 5 pages
FORM OP-20-01-06(0)
FIG. 6

*the way to trust* KCL
Report no.: ES12B19001  TEST REPORT
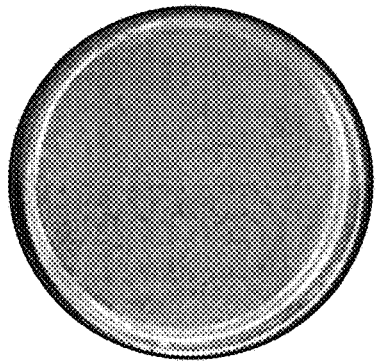
Antibacterial experiment
Blank (24h)
*Staphylococcus ayreus*
ATCC 6538P
[photo 5]
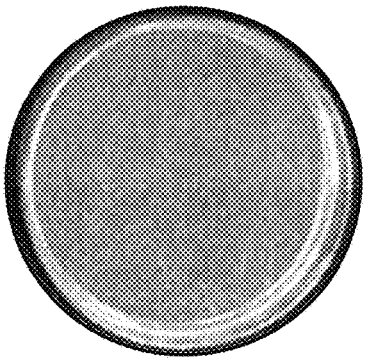
Antibacterial experiment
Antibacterial plastic
(general-untreated)
*Staphylococcus ayreus*
ATCC 6538P
[photo 6]
5 of total 5 pages
FORM OP-20-01-06(0)
FIG. 7

[fig. 8]

KCL TEST REPORT

Report no.: ES12B19002

Test result

| Test Item | | Test result | | | Test method |
|---|---|---|---|---|---|
| | | Initial concentration (CFU/mL) | Concentration after 24 hours (CFU/mL) | Bacterial reduction rate (%) | |
| Antibacterial test by Escherichia coli | BLANK | $3.4 \times 10^5$ | $4.8 \times 10^6$ | - | KCL-FIR-1003 : 2011 |
| | Antibacterial plastic (1%) | $3.4 \times 10^5$ | < 10 | 99.9 | |
| Antibacterial test by Pseudomonas aeruginosa | BLANK | $3.6 \times 10^5$ | $5.0 \times 10^6$ | - | |
| | Antibacterial plastic (1%) | $3.6 \times 10^5$ | < 10 | 99.9 | |
| Antibacterial test by Staphylococcus aureus | BLANK | $2.9 \times 10^5$ | $4.6 \times 10^6$ | - | |
| | Antibacterial plastic (1%) | $2.9 \times 10^5$ | < 10 | 99.9 | |

* CFU : Colony Forming Unit

* Concentration of bacteria inoculum (CFU/mL) : *Escherichia coli* : $3.4 \times 10^5$,
  *Pseudomonas aeruginosa* : $3.6 \times 10^5$,
  *Staphylococcus aureus* : $2.9 \times 10^5$

* strain used : *Escherichia coli* ATCC 8739
  *Pseudomonas aeruginosa* ATCC 15442
  *Staphylococcus aureus* ATCC 6538P

* Test group : 5 cm × 5 cm,
  Control group : Stomacher film : 5 cm × 5 cm

FORM OP-20-01-06(0)

*the way to trust* KCL
Report no.: ES12B19002     TEST REPORT
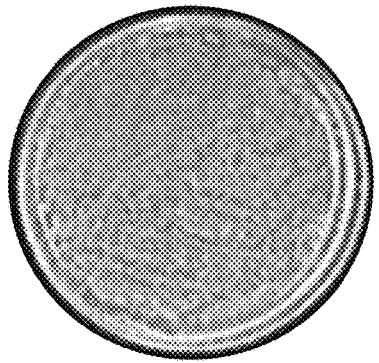
K C L
Antibacterial experiment
Blank (24h)
*Escherichia coli* ATCC 8739
[photo 1]
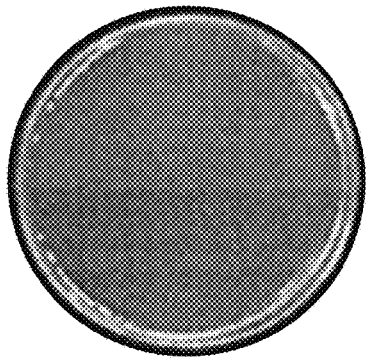
K C L
Antibacterial experiment
Antibacterial plastic
(1%)
*Escherichia coli* ATCC 8739
[photo 2]
3 of total 5 pages
FORM OP-20-01-06(0)
FIG. 9

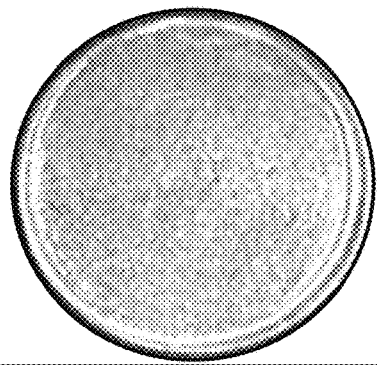
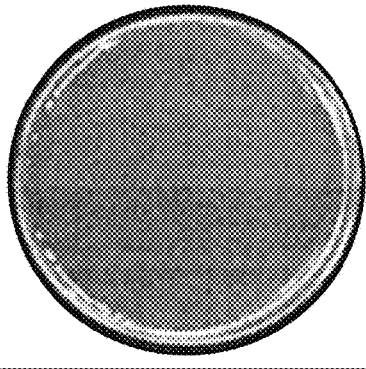
FIG. 10

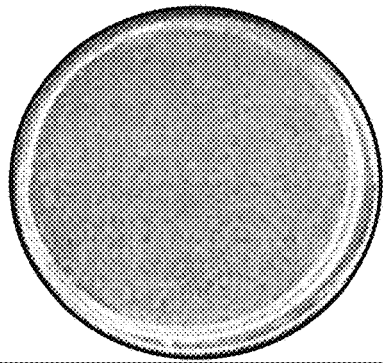
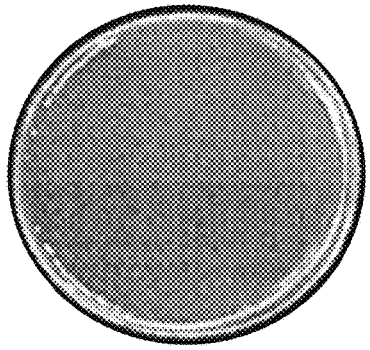
FIG. 11

[fig. 12]

KCL TEST REPORT

*the way to trust*

Report no.: ES12B1XXX

Test result

| Test Item | | Test result | | | Test method |
|---|---|---|---|---|---|
| | | Initial concentration (CFU/mL) | Concentration after 24 hours (CFU/mL) | Bacterial reduction rate (%) | |
| Antibacterial test by Escherichia coli | Blank | $3.4 \times 10^5$ | $4.8 \times 10^6$ | - | KCL-FIR-1003 : 2011 |
| | Antibacterial Silicone (Rubber, TPU)1% | $3.4 \times 10^5$ | < 10 | 99.9 | |
| Antibacterial test by Pseudomonas aeruginosa | Blank | $3.6 \times 10^5$ | $5.0 \times 10^6$ | - | |
| | Antibacterial Silicone (Rubber, TPU)1% | $3.6 \times 10^5$ | < 10 | 99.9 | |
| Antibacterial test by Staphylococcus aureus | Blank | $2.9 \times 10^5$ | $4.6 \times 10^6$ | - | |
| | Antibacterial Silicone (Rubber, TPU)1% | $2.9 \times 10^5$ | < 10 | 99.9 | |

※ CFU : Colony Forming Unit

※ Concentration of bacteria inoculum (CFU/mL) : Escherichia coli : $3.4 \times 10^5$
　　　　　　　　　　　　　　　　　　　　　Pseudomonas aeruginosa : $3.6 \times 10^5$
　　　　　　　　　　　　　　　　　　　　　Staphylococcus aureus : $2.9 \times 10^5$ ※ strain used : Escherichia coli ATCC 8739
　　　　　　　 Pseudomonas aeruginosa ATCC 15442
　　　　　　　 Staphylococcus aureus ATCC 6538P ※ Test group : 5 cm × 5 cm,
　　Control group : Stomacher film : 5 cm × 5 cm

[fig. 13]
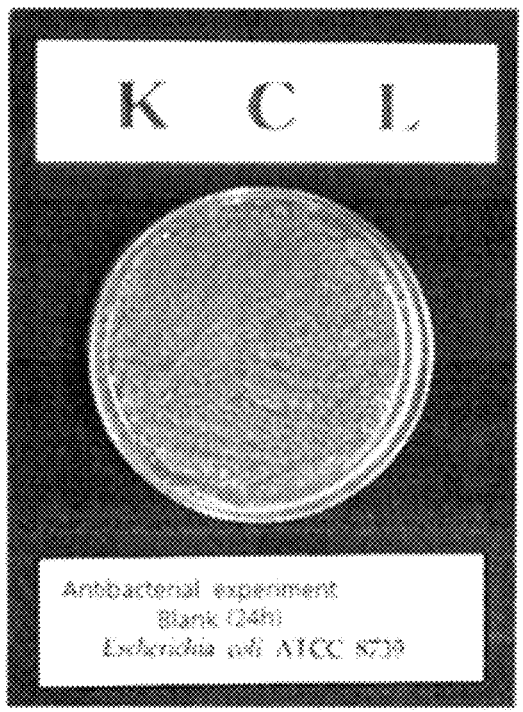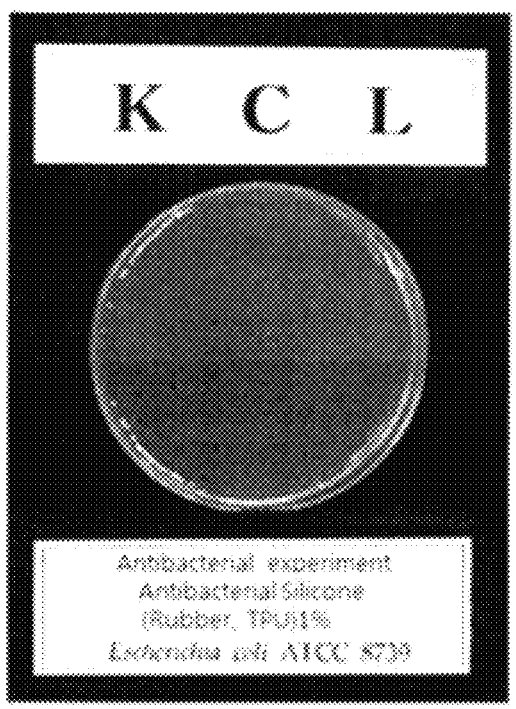

fig. 14
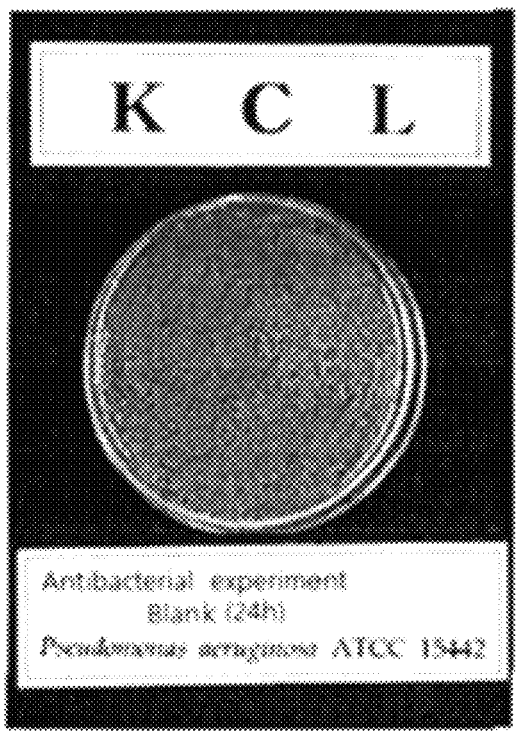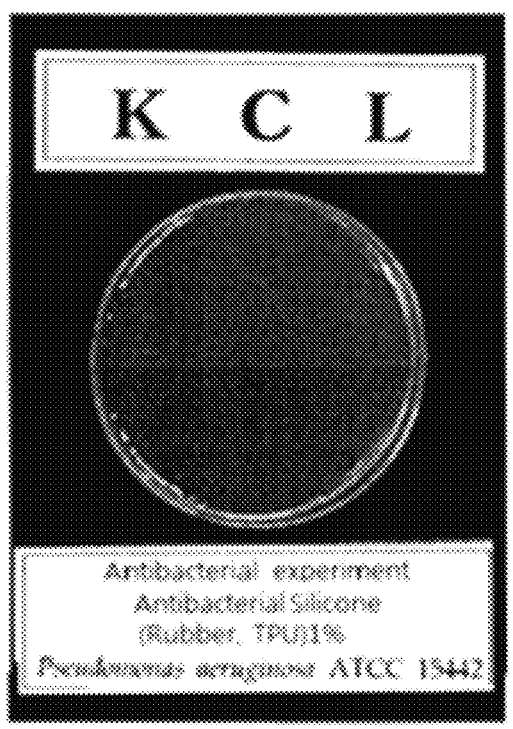

*the way to trust* KCL
TEST REPORT
Report no.: ES12B19005
| K C L | K C L |
|---|---|
| 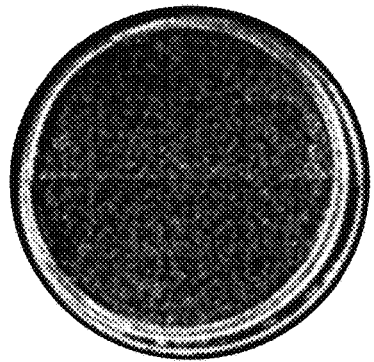 | 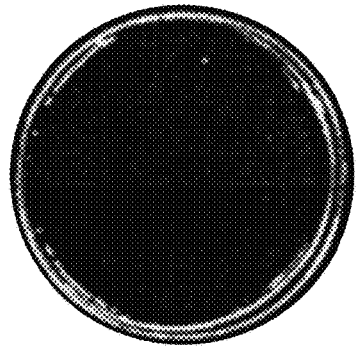 |
| Antibacterial experiment<br>Blank (24h)<br>*Staphylococcus ayreus*<br>ATCC 6538P | Antibacterial experiment<br>Antibacterial Silicone<br>(Rubber, TPU)1%<br>*Staphylococcus ayreus*<br>ATCC 6538P |
| [photo 5] | [photo 6] |
FORM OP-20-01-06(0)
FIG. 15

*the way to trust* KCL
TEST REPORT
Report no.: ES12B19003
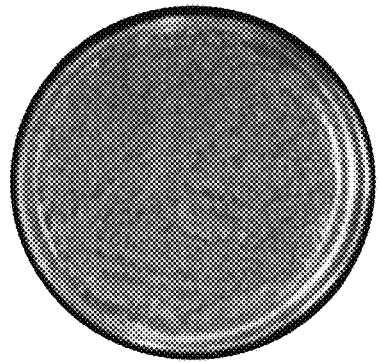
K C L
Antibacterial experiment
Blank (24h)
*Escherichia coli* ATCC 8739
[photo 1]
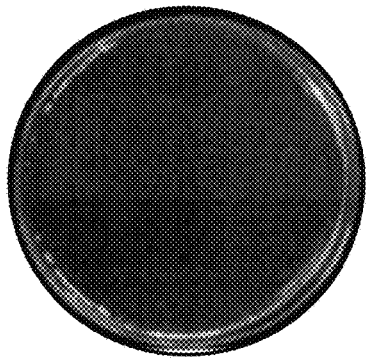
K C L
Antibacterial experiment
Antibacterial plastic
(2%)
*Escherichia coli* ATCC 8739
[photo 2]
3 of total 5 pages
FORM OP-20-01-06(0)
FIG. 16

*the way to trust* KCL
Report no.: ES12B19003
TEST REPORT
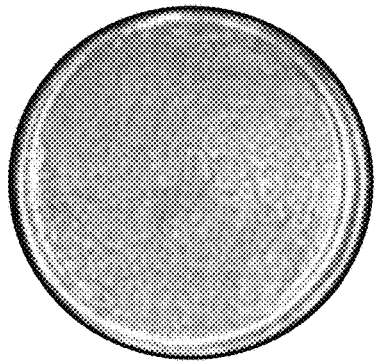
Antibacterial experiment
Blank (24h)
*Pseudomonas aeruginosa*
ATCC 15442
[photo 3]
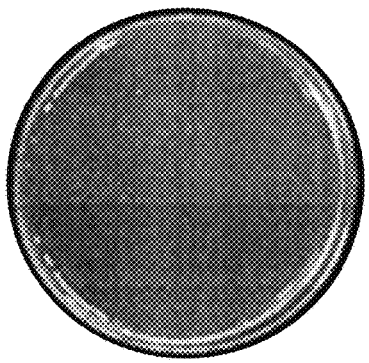
Antibacterial experiment
Antibacterial plastic
(2%)
*Pseudomonas aeruginosa*
ATCC 15442
[photo 4]
4 of total 5 pages
FORM OP-20-01-06(0)
FIG. 17

Sanitary Zipper Bag
Sesame leaf
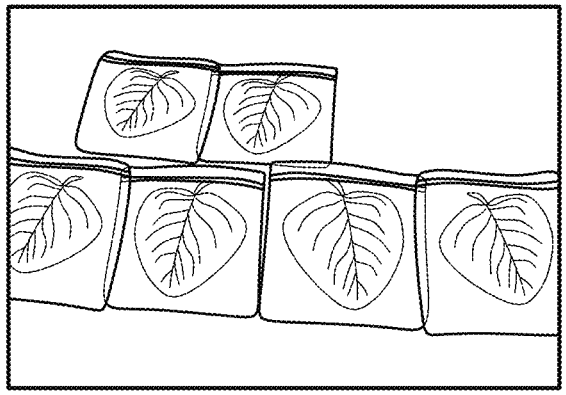
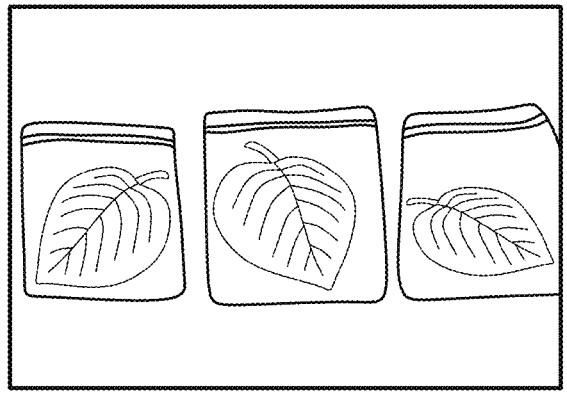
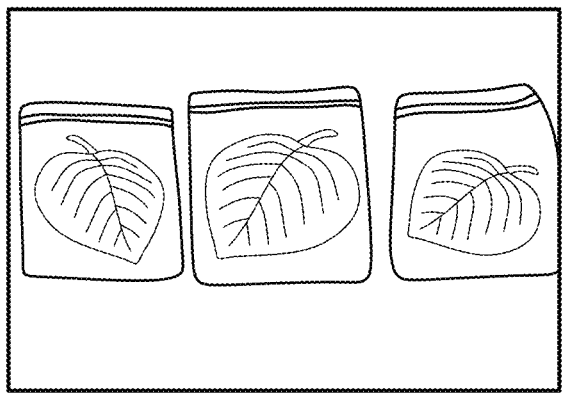
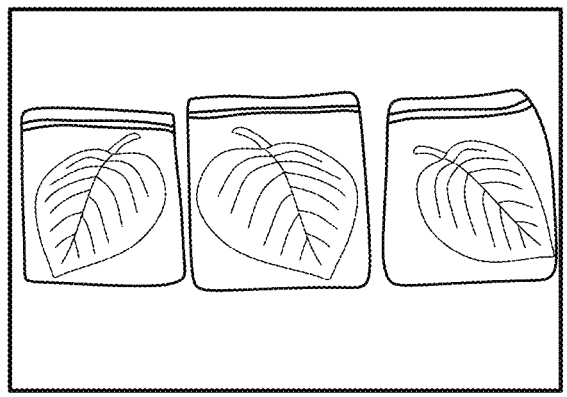
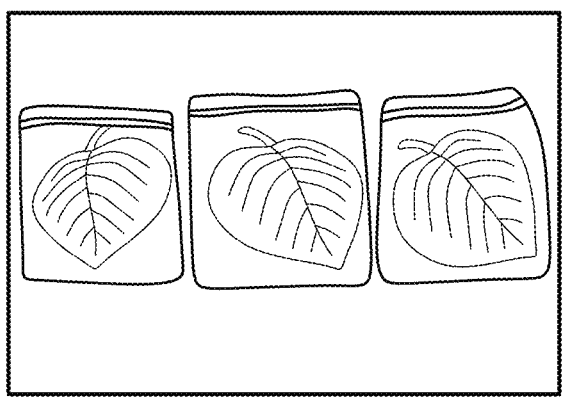
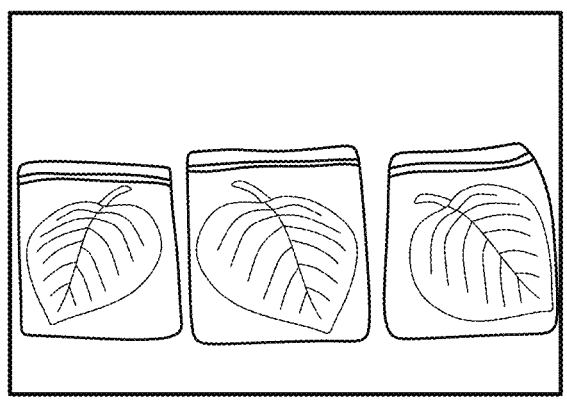
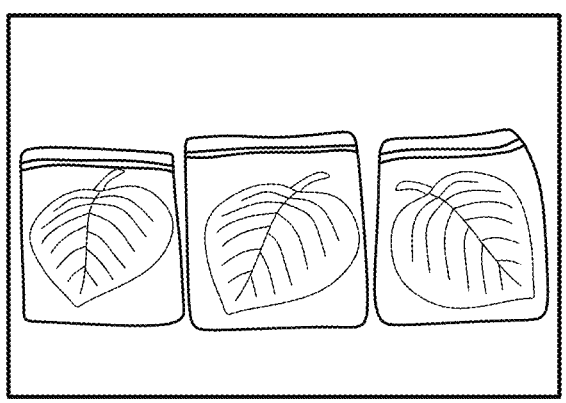
FIG. 18

Sanitary Zipper Bag
Lettuce
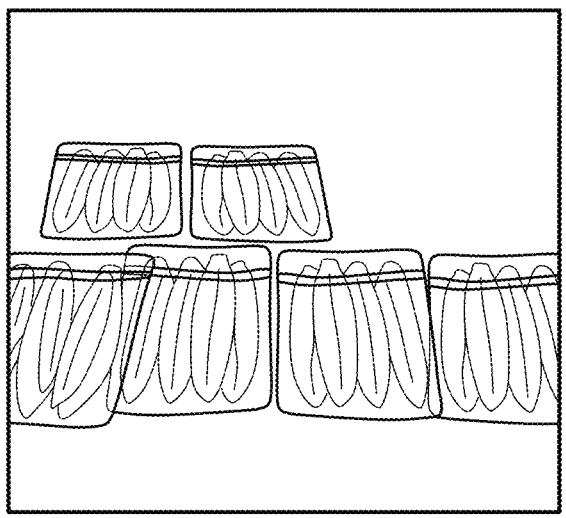
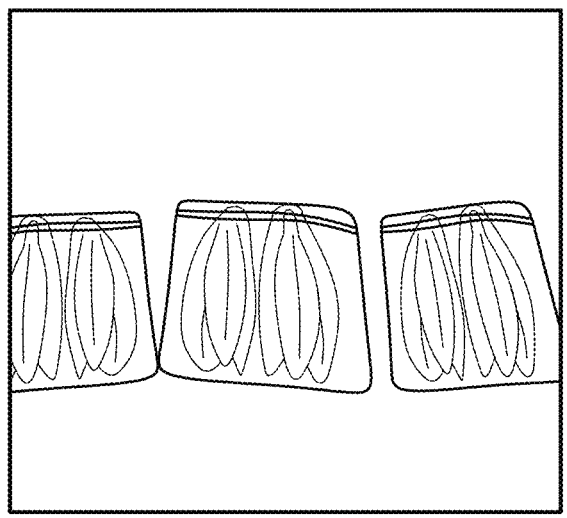
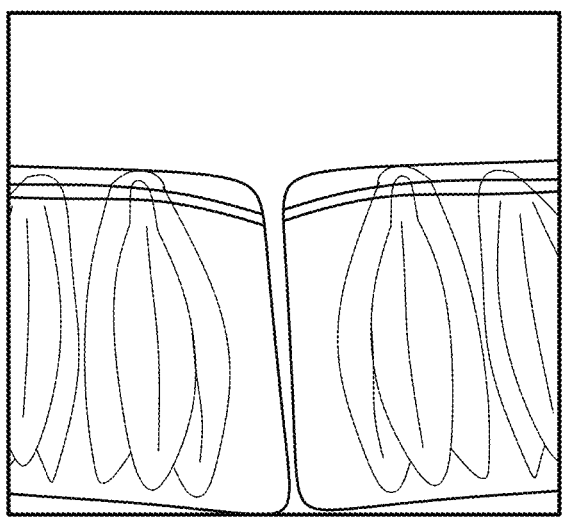
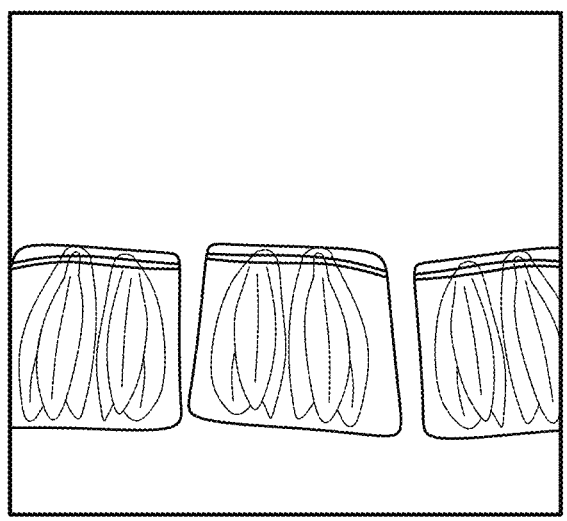
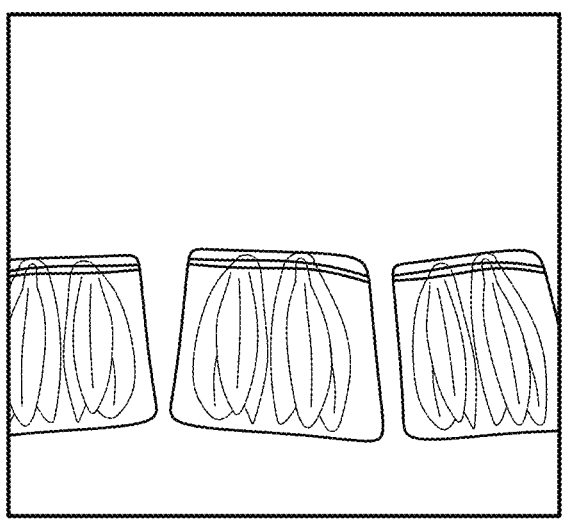
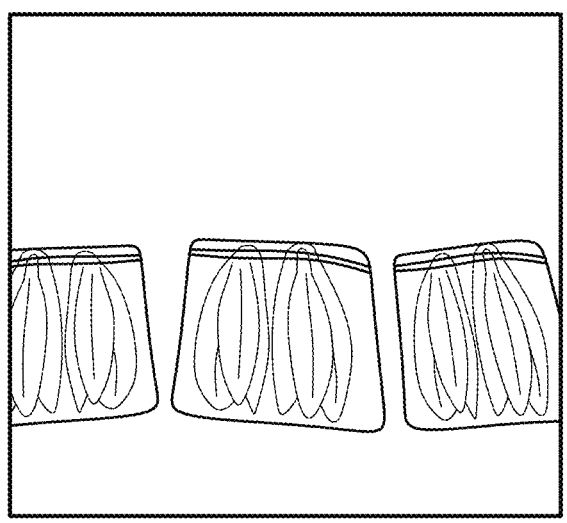
FIG. 19

[ fig 20 ]
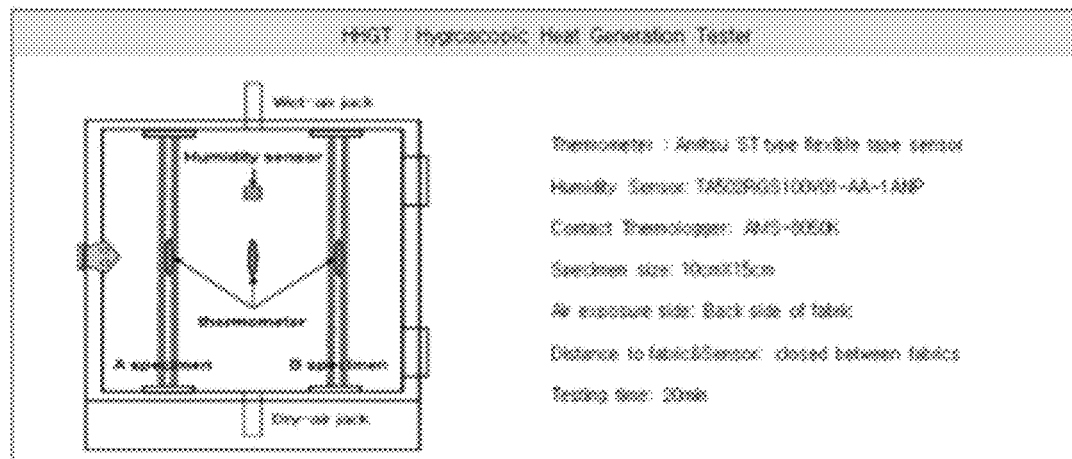

【 fig 21 】
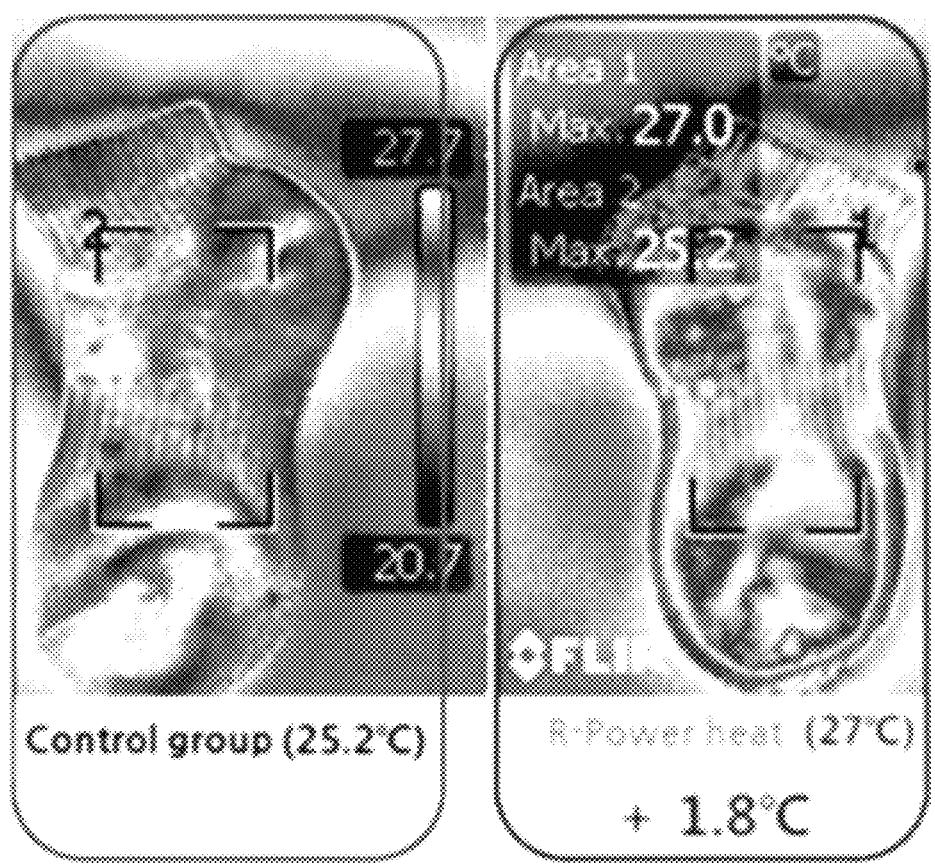

NANOPARTICLE COMPOSITION HAVING ANTIBACTERIAL AND PYROGENIC PROPERTIES AND ITS MANUFACTURING METHOD

BACKGROUND

(a) Technical Field

The present invention relates to a nanoparticle composition with antibacterial and exothermic properties and a manufacturing method thereof, more particularly, a nanoparticle composition with very good antibacterial and exothermic properties obtained by preparing an ionized calcium powder from shells obtained through foreign matter removing, cleaning, drying, sintering, cooling and pulverizing processes, and passing it through a tourmaline mixing stage, a surfactant treatment stage, a synthetic resin mixing stage and a nanoparticle molding stage, and a manufacturing method thereof.

(b) Background Art

In recent years, resin compositions with antibacterial properties, so-called antibacterial resin compositions, are widely used in construction materials, household appliances, general merchandise, packaging materials, food manufacturing facilities, drug manufacturing facilities, medical facilities and the like.

In addition, inorganic antibacterial agents having the higher safety, the longer antibacterial action, and the superior heat resistance as compared with the organic antibacterial agents have been used very favorably as an antibacterial agent which is contained in such antibacterial resin compositions.

Most of these antibacterial technologies can be divided into a technology group that forms a coating film that gives antibacterial power to the surface of most products and a technology group for forming antibacterial products by incorporating materials showing antibacterial performance into a raw material. First, the technology of forming the antibacterial coating film on the surface of the product has a problem that if the coating film is damaged, the antibacterial performance is extinguished together and thus the antibacterial performance itself is not persistent. In addition, the technology of molding the product by incorporating the antibacterial materials into the raw material has an advantage that the antibacterial performance is maintained constantly as compared to the coating technology, but has a problem that the antibacterial power is not sufficiently realized or the manufacture of the product is difficult.

Korean Patent No. 10-0483075 relates to a method for producing a functional calcium oxide, and more particularly, provides a method for preparing the functional calcium oxide comprising a) a stage of primarily sintering calcium-containing materials at a temperature of 1,000° C. to 1,400° C. for 2 to 6 hours; b) a stage of preparing a calcium oxide powder by pulverizing the sintered calcium oxide (CaO); c) a stage of preparing a hydrated lime solution by adding inorganic acid and water to the calcium oxide powder; d) a stage of agitating and aging the hydrated lime solution; e) a stage of filtering and drying the aged hydrated lime solution; and f) a stage of secondarily sintering the dried calcium oxide under the same temperature and time conditions as in the step a), and describes that the functional calcium oxide maintains a stable crystalline state and thus is easy to store, and can be used as a deodorizing agent for decomposing odorous substances and an antibacterial agent for killing various bacteria and fungi by adding various functional metal substances. However, the functional calcium oxide shows functional properties by adding the metal substance to the powder of the functional calcium oxide, and thus even though the antibacterial performance is recognized, there is a problem that it is not verified whether it can be reliably used in food products.

Korean Patent Registration No. 10-0483075 (Apr. 4, 2005)

The above information disclosed in this Background section is only for enhancement of understanding of the background of the invention and therefore it may contain information that does not form the prior art that is already known in this country to a person of ordinary skill in the art.

SUMMARY OF THE DISCLOSURE

Accordingly, the technical problem to be solved in the present invention is to provide a nanoparticle composition with better antibacterial performance by washing the shells with alkaline water and treating the powder after a grinding process with yellow dye and a surfactant.

It is another object of the present invention to provide a manufacturing method for the nanoparticle composition.

It is another object of the present invention to enable the nanoparticle composition to be utilized as the raw material for a master batch and thus to provide a container or a film with deodorization and antibacterial function, which is produced using the master batch as the main raw material and is used to contain food or the like, so that consumers can use it safely.

In addition, it is another object of the present invention to make the nanoparticle composition have exothermicity.

In order to solve the above-mentioned problems and to achieve the objects, the manufacturing method of the nanoparticle composition with antibacterial and exothermic properties of the present invention is composed of an ionized calcium powder preparing stage of preparing an ionized calcium powder using shells as the raw material (S1); a tourmaline mixing stage of mixing the ionized calcium powder with tourmaline powder having a particle size of 3-8 μm at a weight ratio of 0.01 to 2 wt. % (S2); a surfactant treatment stage of lowering the surface polarity of the inorganic material powder particles by surface treating the inorganic material powder particles made in the tourmaline mixing stage with a cationic surfactant (S3); a synthetic resin mixing stage of mixing 1-50 wt. % of the powder obtained through the surfactant treatment stage with a synthetic resin comprising any one selected from polyethylene, polypropylene, polyurethane, ABS (acrylonitrile-butadiene-styrene resin), mirrorable type silicone rubber, and polyurethane rubber (TPU: thermoplastic polyurethane) which are treated to contain 1-5 wt. % of the natural antibacterial agent respectively (S4); and a nanoparticle molding stage of molding the resultant obtained through the synthetic resin mixing stage into a nanoparticle (S5).

The ionized calcium powder preparing stage (S1) is composed of a shell injecting process (S10); a foreign substance removing process (S11); a cleaning process (S12); a drying process (S13); a sintering process (S14); a cooling process for quenching the rough shell passed through the sintering process to room temperature (S15); and a pulverizing process for pulverizing the particle size into the size of 3-8 μm (S16).

It is characterized in that the foreign substance removing process (S11) and the cleaning process (S12) are performed three times in succession, the cleaning process S12 uses an ultrasonic cleaning method using frequencies above the audible frequency, and the cleaning is performed using alkaline water of pH 8.5-9.0.

The sintering process (S14) uses a cylindrical sintering furnace having a downward inclination, rotating by a driving device and maintaining a high temperature, wherein when the purity of calcium is 99% or more, the rotational speed of the sintering furnace is 30 to 35 rpm, the amount of shell is 300 kg/hr., and the sintering temperature is 1,200° C. or more, it is made by keeping the shell in the sintering furnace for 45 to 90 minutes.

It is characterized in that the cationic surfactant used in the surfactant treatment stage (S3) has a purity of 99%, has 12-20 carbon atoms, and is any one of CTAB (cetyl trimethylammonium bromide) and CTAC (cetyl trimethylammonium chloride).

The alkaline water is characterized by being prepared by passing the underground water through a filter which is made by filling a powder of cockles into a mesh with micropores.

The polyethylene is characterized by being one of LLDPE (Linear LDPE), HDPE and LDPE.

The pulverizing process (S16) includes a process of coating the surface of the ground powder in a spraying manner with a composition formed by containing 0.1 wt. % to 1 wt. % of yellow dye and filling with the cationic surfactant as the remainder.

The polyethylene is characterized by being prepared using one or a mixture of two or more selected from spearmint extract, essential oil, grapefruit seed extract, phytoncide, evening primrose extract, juniper leaf extract, bamboo leaf extract, pine leaf extract, tree of heaven leaf extract, ginkgo leaf extract, *salvia* extract, cranesbill extract, and a solution of violacein diluted to 1% concentration in ethanol.

Another feature of the invention is in the nanoparticle composition itself produced by the above manufacturing method.

Since the nanoparticle composition prepared by the manufacturing method of the nanoparticle composition with the antibacterial property and the exothermicity using the ionized calcium powder of the present invention has superior antibacterial performance due to the addition of the yellow dye with excellent antibacterial performance and the cationic surfactant, and at the same time, uses natural materials such as the shell of the cockles and the like, and precisely removes foreign substance by introducing an ultrasonic cleaning method, thus it can be safely used as a container and the like for food or the like.

Additionally, by reusing untreated and discarded shells from cockle, oyster or the like which is local specialties, it can contribute to the utilization of effective resources and the resolution of environmental problems.

In addition, the present invention allows the nanoparticle composition itself to have exothermicity so that a plastic container or glove or fabric made of materials prepared using the nanoparticle composition as the raw material can be used pleasantly by the user.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein:

FIG. 1 is a diagram schematically illustrating the manufacturing method of the nanoparticle composition with antibacterial and exothermic properties according to the present invention.

FIG. 2 is a diagram schematically showing a process for preparing the ionized calcium powder.

FIG. 3 is a photograph of a master batch chip prepared using the nanoparticle composition having antibacterial and exothermic properties of the present invention as the raw material.

FIG. 4 is test report obtained from Korea Conformity Laboratories (KCL) for the antibacterial experiments of the general antibacterial plastics.

FIG. 5 is test report obtained from Korea Conformity Laboratories (KCL) for the antibacterial Experiment of *Escherichia coli*.

FIG. 6 is test report obtained from Korea Conformity Laboratories (KCL) for the antibacterial Experiment of *Pseudomonas aeruginosa*.

FIG. 7 is test report obtained from Korea Conformity Laboratories (KCL) for the antibacterial Experiment of *Staphylococcus aureus*.

FIG. 8 is test report obtained from Korea Conformity Laboratories (KCL) for the antibacterial experiments of the films made from the master batches using the nanoparticle compositions prepared by the present invention as the raw material.

FIG. 9 is test report obtained from Korea Conformity Laboratories (KCL) for the antibacterial Experiment of *Escherichia coli*.

FIG. 10 is test report obtained from Korea Conformity Laboratories Experiment of *Pseudomonas aeruginosa*.

FIG. 11 is test report obtained from Korea Conformity Laboratories (KCL) for the antibacterial Experiment of *Staphylococcus aureus*.

FIG. 12 is test report obtained from Korea Conformity Laboratories (KCL) for the antibacterial Experiments of the silicone rubbers made from the master batches using the nanoparticle compositions prepared by the present invention as the raw material.

FIG. 13 is test report obtained from Korea Conformity Laboratories (KCL) for the antibacterial Experiment of *Escherichia coli*.

FIG. 14 is test report obtained from Korea Conformity Laboratories (KCL) for the antibacterial Experiment of *Pseudomonas aeruginosa*.

FIG. 15 is test report obtained from Korea Conformity Laboratories (KCL) for the antibacterial Experiment of *Staphylococcus aureus*.

FIG. 16 is test report obtained from Korea Conformity Laboratories (KCL) for the antibacterial Experiment—*Escherichia coli* ATCC 8739 of the plastic containers made from the master batches using the nanoparticle compositions prepared by the present invention as the raw material.

FIG. 17 is test report obtained from Korea Conformity Laboratories (KCL) for the antibacterial Experiment of *Pseudomonas aeruginosa*.

FIG. 18 is photographs showing experimental results of the additional antibacterial experiments on the sanitary zipper bag films with Sesame leaf made from master batches using the nanoparticle compositions prepared by the present invention.

FIG. 19 is photographs showing experimental results of the additional Antibacterial experiments on the sanitary zipper bag films with lettuce made from master batched using the nanoparticle composition prepared by the present invention as the raw material.

FIG. 20 is an exothermic test reports of the fabric comprising the nanoparticle compositions prepared by the present invention as the raw material.

FIG. 21 is the photo of the showing temperature difference.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The name of the invention is "Nanoparticle Composition Having Antibacterial and Pyrogenic Properties and Its Manufacturing Method," and is described in detail so that it can be easily recognized by an ordinary technician, and additional descriptions that are sufficiently inferable are omitted and, if necessary, examples and drawings are described. Also, the terms defined in the present specification and claims should not be construed as limiting, but may vary depending on the intentions or customs of the operator, and should be construed as meaning and concept consistent with the technical idea of the present invention.

In one aspect of the present invention,

FIG. 1 is a diagram schematically illustrating the manufacturing method of the nanoparticle composition with antibacterial and exothermic properties according to the present invention, FIG. 2 is a diagram schematically showing a process for preparing the ionized calcium powder, FIG. 3 is a photograph of a master batch chip prepared using the nanoparticle composition having antibacterial and exothermic properties of the present invention as the raw material, FIGS. 4 to 7 are test reports obtained from Korea Conformity Laboratories (KCL) for the antibacterial experiments of the general antibacterial plastics, FIGS. 8 to 11 are test reports obtained from Korea Conformity Laboratories (KCL) for the antibacterial experiments of the films made from the master batches using the nanoparticle compositions prepared by the present invention as the raw material, FIGS. 12 to 15 are test reports obtained from Korea Conformity Laboratories (KCL) for the antibacterial experiments of the silicone rubbers made from the master batches using the nanoparticle compositions prepared by the present invention as the raw material, FIGS. 16 and 17 are test reports obtained from Korea Conformity Laboratories (KCL) for the antibacterial experiments of the plastic containers made from the master batches using the nanoparticle compositions prepared by the present invention as the raw material, FIGS. 18 and 19 are photographs showing experimental results of the additional antibacterial experiments on the films made from master batches using the nanoparticle compositions prepared by the present invention as the raw material, FIGS. 20 to 22 are an exothermic test reports of the fabric comprising the nanoparticle compositions prepared by the present invention as the raw material. Referring to FIG. 1, the manufacturing method of the nanoparticle composition with antibacterial and exothermic properties of the present invention is composed of an ionized calcium powder preparing stage of preparing an ionized calcium powder using shells as the raw material (S1); a tourmaline mixing stage of mixing the ionized calcium powder with tourmaline powder having a particle size of 3-8 μm at a weight ratio of 0.01 to 2 wt. % (S2); a surfactant treatment stage of lowering the surface polarity of the inorganic material powder particles by surface treating the inorganic material powder particles made in the tourmaline mixing stage with a cationic surfactant (S3); a synthetic resin mixing stage of mixing 1-50 wt. % of the powder obtained through the surfactant treatment stage with a synthetic resin comprising any one selected from polyethylene, polypropylene, polyurethane, ABS (acrylonitrile-butadiene-styrene resin), mirrorable type silicone rubber, and polyurethane rubber (TPU: thermoplastic polyurethane) which are treated to contain 1-5 wt. % of the natural antibacterial agent respectively (S4); and a nanoparticle molding stage of molding the resultant obtained through the synthetic resin mixing stage into a nanoparticle (S5).

The mixing purpose of the tourmaline powder in the tourmaline mixing stage (S2) is to make the nanoparticle composition, which is the final product, emit far-infrared rays to show the exothermic effect.

It is characterized in that the cationic surfactant used in the surfactant treatment stage (S3) has a purity of 99%, has 12-20 carbon atoms, and is any one of CTAB (cetyl trimethylammonium bromide) and CTAC (cetyl trimethylammonium chloride).

The cationic surfactant should be harmless to the human body.

The natural antibacterial agent is characterized by being prepared using one or a mixture of two or more selected from spearmint extract, essential oil, grapefruit seed extract, phytoncide, evening primrose extract, juniper leaf extract, bamboo leaf extract, pine leaf extract, tree of heaven leaf extract, ginkgo leaf extract, *salvia* extract, cranesbill extract, and a solution of violacein diluted to 1% concentration in ethanol.

One embodiment relating to the extraction of the natural antibacterial agent, that is, the extraction of antibacterial substance from ginkgo leaf can be obtained through the following procedure. After the ginkgo leaves are dried, the ginkgo leaves are cut to an appropriate size using a knife or a cutting device (for example, knife, vegetable cutter, etc.), the extraction solvent selected from water and lower alcohol (or a mixed solvent of lower alcohol and water) corresponding to 1 to 15 times of the weight of the ginkgo leaves is added to extract the antibacterial component by immersing at a constant temperature (for example, 10 to 30° C.) for a predetermined period of time (for example, 5 to 10 days), and then, the extracted antibacterial solvent can be concentrated with a vacuum concentrator to obtain an antibacterial extract.

It is preferable that the mixed solution of violacein in the natural antibacterial agent is aged at room temperature for 12 to 36 hours after stirring for 1 to 3 hours and then used.

In an embodiment where the natural antibacterial agent is mixed with a synthetic resin to produce a mixture, treatment of 2.0 wt. % of the pine leaf extract relative to the weight to a mirrorable type silicone rubber can be produced by a method of adding to a high-speed stirrer and stirring at 400 rpm.

The polyethylene is characterized by being one of LLDPE (Linear LDPE), HDPE and LDPE.

Referring to FIG. 2, the ionized calcium powder preparing stage (S1) is composed of a shell injecting process (S10); a foreign substance removing process (S11); a cleaning process (S12); a drying process (S13); a sintering process (S14); a cooling process for quenching the rough shell passed through the sintering process to room temperature (S15); and a pulverizing process for pulverizing the particle size into the size of 3-8 µm (S16).

It is characterized in that the foreign substance removing process (S11) and the cleaning process (S12) are performed three times in succession, the cleaning process S12 uses an ultrasonic cleaning method using frequencies above the audible frequency, and the cleaning is performed using alkaline water of pH 8.5-9.0.

The alkaline water is characterized by being prepared by passing the underground water through a filter which is made by filling a powder of cockles into a mesh with micropores.

The alkaline water not only plays an important role in naturally naturalizing due to the containing of a large amount of potassium, magnesium, sodium and iron, but also may exhibit a bactericidal effect against a shell contaminated with various pollution or the like.

Meanwhile, the alkaline water-producing powder is a mixture containing 98% of a powder of cockles and the rest filled with a shell powder such as a mussel shell, an oyster shell, etc., and the mixture of 35 to 50 wt. % of an illite powder, 12 to 30 wt. % of a zeolite powder, 2 to 20 wt. % of a shell powder and 1 to 20 wt. % of a coral powder can be used.

The sintering process (S14) uses a cylindrical sintering furnace having a downward inclination, rotating by a driving device and maintaining a high temperature, wherein when the purity of calcium is 99% or more, the rotational speed of the sintering furnace is 30 to 35 rpm, the amount of shell is 300 kg/hr., and the sintering temperature is 1,200° C. or more, it is made by keeping the shell in the sintering furnace for 45 to 90 minutes.

The pulverizing process (S16) includes a process of coating the surface of the ground powder in a spraying manner with a composition formed by containing 0.1 wt. % to 1 wt. % of yellow dye and filling with the cationic surfactant as the remainder.

The yellow dye used in the pulverizing process has been used as a rare paint for the golden color of emperor's armor, helmet and other metal ornaments since the epoch of the three Kingdoms. Ben Cao Gang Mu (Compendium of Materia *Medica*) records that the yellow dye tree is effective in removing fever, treating eye diseases and burns, and effective against leprosy, and is harmless. It is preferable that the yellow dye in the present invention is extracted and purified by mainly extracting from seeds of the yellow dye tree with 70% ethanol, and sequentially fractionating with hexane, ethyl acetate and butanol, which are solvents different in polarity, and then used.

It is known that ethyl acetate fraction and nucleic acid fraction of this yellow dye purified water have excellent antibacterial activity.

FIG. 3 is a photograph of the master batch chip made by the manufacturing method of the nanoparticle composition with antibacterial and exothermic properties.

The antibacterial master batch prepared using the nanoparticle composition as the raw material can be applied to the production of various living containers and industrial containers, such as various antibacterial lunch boxes, side dish cases, trash cans, and water bottles.

The antibacterial film produced by using the master batch chip as the raw material can be allied to produce daily necessities, such as antibacterial disposable gloves, wraps, rolls, zipper bags, and rubber gloves, and can also be applied to all plastic bags, such as snack packs, Ramen bags, etc.

In addition, Any one layer of multi-layered fabrics treated the nanoparticle composition is possible to cause to be exothermic by allowing it to react with moisture in the human body or air.

Example 1

Antibacterial Experiment of a General Antibacterial Plastic without Shell and Yellow Dye Treatment A generally and commercially available antibacterial plastic was used as a 5 cm×5 cm specimen and an untreated stomacher film with the same size was used as the control group. *Escherichia coli* (strain: *Escherichia coli* ATCC 8739, initial concentration $3.4\times10^5$ CFU/mL), *Pseudomonas aeruginosa* (strain: *Pseudomonas aeruginosa* ATCC 15442, initial concentration $3.6\times10^5$ CFU/mL), *Staphylococcus aureus* (strain: *Staphylococcus aureus* ATCC 6538P, initial concentration $2.9\times10^5$ CFU/mL) was used as the inoculum. After holding at room temperature for 24 hours, the degree of initial concentration change was observed.

Table 1 below shows the results, and formal test reports are shown in FIGS. 4 to 7.

TABLE 1

| Test Item | | Initial concentration (CFU/mL) | Concentration after 24 hours (CFU/mL) | Bacterial reduction rate (%) |
|---|---|---|---|---|
| Antibacterial test by *Escherichia coli* | Blank | $3.4\times10^5$ | $4.8\times10^5$ | — |
| | Untreated general antibacterial plastic | $3.4\times10^5$ | $4.7\times10^5$ | 2.0 |
| Antibacterial test by *Pseudomonas aeruginosa* | Blank | $3.6\times10^5$ | $5.0\times10^5$ | — |
| | Untreated general antibacterial plastic | $3.6\times10^5$ | $4.8\times10^5$ | 4.0 |
| Antibacterial test by *Staphylococcus aureus* plastic | Blank | $2.9\times10^5$ | $4.6\times10^5$ | — |
| | Untreated general antibacterial | $2.9\times10^5$ | $4.5\times10^5$ | 2.1 |

It can be confirmed that the antibacterial effect of the generally and commercially available antibacterial plastic was unexpectedly insignificant.

Example 2

The Antibacterial Experiment of the Film Prepared Using the Nanoparticle Composition Prepared by the Manufacturing Method of the Present Invention as the Raw Material A specimen containing 1% of the nanoparticle composition, which is a film prepared using the nanoparticle composition prepared by the present invention as the raw material (contained the ionized calcium powder in an amount of 1.485% by weight, contained the tourmaline powder in an amount of 0.015% by weight, and treated with phytoncide as a natural antibacterial agent), was used as a 5 cm×5 cm specimen, and an untreated stomacher film with the same size was used as the control group. *Escherichia coli* (strain: *Escherichia coli* ATCC 8739, initial concentration $3.4\times10^5$ CFU/mL), *Pseudomonas aeruginosa* (strain: *Pseudomonas aeruginosa* ATCC 15442, initial concentration $3.6\times10^5$ CFU/mL), *Staphylococcus aureus* (strain: *Staphylococcus aureus* ATCC 6538P, initial concentration $2.9\times10^5$ CFU/ mL) was used as the inoculum. After holding at room temperature for 24 hours, the degree of initial concentration change was observed.

Table 2 below shows the results, and formal test reports are shown in FIGS. 8 to 11.

TABLE 2

| Test item | | Initial concentration (CFU/mL) | Concentration after 24 hours (CFU/mL) | Bacterial reduction rate (%) |
|---|---|---|---|---|
| Antibacterial test by *Escherichia coli* | Blank | $3.4 \times 10^5$ | $4.8 \times 10^5$ | — |
| | Antibacterial plastic (1% containing) | $3.4 \times 10^5$ | <10 | 99.9 |
| Antibacterial test by *Pseudomonas aeruginosa* | Blank | $3.6 \times 10^5$ | $5.0 \times 10^5$ | — |
| | Antibacterial plastic (1% containing) | $3.6 \times 10^5$ | <10 | 99.9 |
| Antibacterial test by *Staphylococcus aureus* | Blank | $2.9 \times 10^5$ | $4.6 \times 10^5$ | — |
| | Antibacterial plastic (1% containing) | $2.9 \times 10^5$ | <10 | 99.9 |

From this example, it can be seen that the antibacterial effect of the film prepared from the nanoparticle composition prepared by the present invention is very remarkable. It is recognized that these antibacterial effects are expressed by high alkalinity and OH-action, higher anion and ultraviolet emissivity than other materials, and high specific surface area due to the nature of the porous particles, and also the injection of the purified water of yellow dye and the natural antibacterial agent which have excellent antibacterial properties.

Example 3

The Antibacterial Experiment of the Antibacterial Silicone Rubber Prepared Using the Nanoparticle Composition Prepared by the Manufacturing Method of the Present Invention as the Raw Material A specimen containing 1% of the ionized calcium powder, which is an antibacterial silicone rubber prepared using the nanoparticle composition prepared by the present invention as the raw material (contained the ionized calcium powder in an amount of 2.97% by weight, contained the tourmaline powder in an amount of 0.03% by weight, and treated with phytoncide as a natural antibacterial agent), was used as a specimen of 5 cm×5 cm, and an untreated stomacher film with the same size was used as the control group. *Escherichia coli* (strain: *Escherichia coli* ATCC 8739, initial concentration $3.4 \times 10^5$ CFU/mL), *Pseudomonas aeruginosa* (strain: *Pseudomonas aeruginosa* ATCC 15442, initial concentration $3.6 \times 10^5$ CFU/mL), *Staphylococcus aureus* (strain: *Staphylococcus aureus* ATCC 6538P, initial concentration $2.9 \times 10^5$ CFU/mL) was used as the inoculum. After holding at room temperature for 24 hours, the degree of initial concentration change was observed.

Table 3 below shows the results, and formal test reports are shown in FIGS. 12 to 15.

TABLE 3

| Test item | | Initial concentration (CFU/mL) | Concentration after 24 hours (CFU/mL) | Bacterial reduction rate (%) |
|---|---|---|---|---|
| Antibacterial test by *Escherichia coli* | Blank | $3.4 \times 10^5$ | $4.8 \times 10^5$ | — |
| | Antibacterial silicone (2% containing) | $3.4 \times 10^5$ | <10 | 99.9 |
| Antibacterial test by *Pseudomonas aeruginosa* | Blank | $3.6 \times 10^5$ | $5.0 \times 10^5$ | — |
| | Antibacterial silicone (2% containing) | $3.6 \times 10^5$ | <10 | 99.9 |
| Antibacterial test by *Staphylococcus aureus* | Blank | $2.9 \times 10^5$ | $4.6 \times 10^5$ | — |
| | Antibacterial silicone (2% containing) | $2.9 \times 10^5$ | <10 | 99.9 |

From this example, it can be seen that the antibacterial effect of the silicone rubber prepared using the nanoparticle composition prepared by the present invention as the raw material is very remarkable.

Example 4

The Antibacterial Experiment of the Plastic Container Prepared Using the Nanoparticle Composition Prepared by the Manufacturing Method of the Present Invention as the Raw Material A plastic container prepared using the nanoparticle composition prepared by the present invention as the raw material (contained 2.97% by weight of ionized calcium powder, contained 0.03% by weight of tourmaline powder, and treated with phytoncide as the natural antibacterial agent) was used as a test group wherein 1 liter of tap water was filled in the container and the test strain was inoculated. A general antibacterial plastic as the control specimen was measured for bacterial reduction rate for 1-5 days under the above conditions. *Escherichia coli* (strain: *Escherichia coli* ATCC 25922, initial concentration $4.5 \times 10^4$ CFU/mL) was used as the inoculum.

Table 4 below shows the results, and formal test reports are shown in FIGS. 16 and 17.

TABLE 4

| Test item | | Initial concentration (CFU/mL) | Concentration after 1 day (CFU/mL) | Concentration after 2 days (CFU/mL) | Concentration after 3 days (CFU/mL) | Concentration after 4 days (CFU/mL) | Concentration after 5 days (CFU/mL) |
|---|---|---|---|---|---|---|---|
| Antibacterial test by *Escherichia* | Blank | $4.5 \times 10^4$ | $3.9 \times 10^4$ | $3.1 \times 10^4$ | $2.3 \times 10^4$ | $1.8 \times 10^4$ | $1.2 \times 10^4$ |
| | Plastic container | $4.5 \times 10^4$ | $3.8 \times 10^4$ | $3.0 \times 10^4$ | $2.2 \times 10^4$ | $1.6 \times 10^4$ | $1.0 \times 10^4$ |

TABLE 4-continued

|  | Test item | Initial concentration (CFU/mL) | Concentration after 1 day (CFU/mL) | Concentration after 2 days (CFU/mL) | Concentration after 3 days (CFU/mL) | Concentration after 4 days (CFU/mL) | Concentration after 5 days (CFU/mL) |
|---|---|---|---|---|---|---|---|
| coli | (2%) Bacterial reduction rate (%) | — | 2.5 | 3.2 | 4.3 | 11.1 | 16.6 |

From this example, it can be seen that the plastic container prepared using the nanoparticle composition prepared by the present invention as the raw material has better antibacterial effect than the general antibacterial plastic container and also that considering that the antibacterial effect is generally lower as compared with Examples 2 to 3, the antibacterial effect is actively generated on the surface of the plastic container.

In the case of the plastic container prepared using the nanoparticle composition prepared by the present invention as the raw material, since the antibacterial activity is active only on the surface of the container, if kimchi is contained in it, it can be prevented from being over fermented and quickly ripened, and it has the advantage that Kimchi can have crispy texture as it is.

Example 5

The Additional Antibacterial Experiment of the Film Prepared Using the Nanoparticle Composition Prepared by the Present Invention as the Raw Material This experiment is intended to demonstrate the results of Example 2 more clearly. A zipper bag made of the film containing 1.5% of ionized calcium powder and a zipper bag made of the film containing 2% of ionized calcium powder were used as test groups respectively (two left sides in the photographs of FIGS. 18 and 19), and a general zipper bag (a product from Lotte in Korea) was used as a control group (the right one in the photographs of FIGS. 18 and 19). Sesame leaf and lettuce (a local food product at Yeosu in Korea) were put into each zipper bag and the changes were observed over time while photographing one time at the same time every day. The temperature was maintained in the range of 26-32° C.

Referring to FIGS. 18 and 19, it can be seen that the zipper bag of the test group was not changed over time, whereas the sesame leaves and lettuce contained in the general zipper bag of the control group were spoiled over time.

Example 6

The Exothermic Test of the Fabric Prepared by Treating the Surface Layer of the Nanoparticle Composition Produced by the Present Invention This experiment is to prove that the nanoparticle composition produced by the present invention reacts with moisture in the air to exert an exothermic effect. (See to FIGS. 20 to 22)

In the Experimental group, the nanoparticle composition was treated with a weight ratio of 2(Nanoparticle Comp):8 (PE) to the polyester portion in fabrics mixed cotton (20%) and polyester (80%), and the control group uses a general fabric mixed (20%) and polyester (80%).

Experiments were carried out by observing the temperature changes in the test group and the control group by spraying in air at room temperature (25° C., 35% humidity) for 20 minutes.

As a result of the experiment, the temperature of the fabric surface of the test group was 1.8° C. higher than that of the control group.

Thus, the exothermic effect or hygroscopic exothermic effect of the fabric using the nanoparticle composition prepared by the present invention was confirmed.

TABLE 5

| Time(min) | #1(° C.) | #2(%) | Difference(° C.) |
|---|---|---|---|
| Initial(T0)[00:00] | 24.6 | 24.7 | 0.1 |
| Max(Tm)[20:00] | 27.5 | 29.3 | 1.8 |
| TemperatureRise(° C.) | 2.9 | 4.6 | 1.7 |

According to the present invention, since the nanoparticle composition prepared by the manufacturing method of the nanoparticle composition with the antibacterial property and the exothermicity using the ionized calcium powder of the present invention has superior antibacterial performance due to the addition of the yellow dye with excellent antibacterial performance and the cationic surfactant, and at the same time, uses natural materials such as the shell of the cockles and the like, and precisely removes foreign substance by introducing an ultrasonic cleaning method, thus it can be safely used as a container and the like for food or the like.

Additionally, by reusing untreated and discarded shells from cockle, oyster or the like which is local specialties, it can contribute to the utilization of effective resources and the resolution of environmental problems.

In addition, the present invention allows the nanoparticle composition itself to have exothermicity so that a plastic container or glove or fabric made of materials prepared using the nanoparticle composition as the raw material can be used pleasantly by the user.

DESCRIPTION OF REFERENCE NUMERALS

S1: ionized calcium powder preparing stage
S10: shell injecting process
S11: foreign substance removing process
S12: cleaning process
S13: drying process
S14: sintering process
S15: cooling process
S16: pulverizing process
S2: a tourmaline mixing stage
S3: surfactant treatment stage
S4: a synthetic resin mixing stage S5: nanoparticle molding stage Embodiments of the disclosed technology can be used to coat any of the following items: wall paper, flooring (wood), laminated wood (the coating placed into the laminate), paint (mixed into the paint), antibacterial socks, vinyl gloves, plastic bags, lunch boxes, face masks, disposble gown for doctors and patients, diapers, non-woven, woven and knitted fabrics.

What is claimed is:

1. A manufacturing method of a nanoparticle composition with antibacterial and exothermic properties, comprising steps of, in order:
    preparing an ionized calcium powder using mussel, oyster, or cockle shells as the raw material;
    mixing the ionized calcium powder with tourmaline powder having a particle size of 3-8 μm producing inorganic material powder particles;
    lowering the surface polarity of the inorganic material powder particles by surface treating the inorganic material powder particles with a cationic surfactant producing a surfactant treatment product;
    mixing the surfactant treatment product with a synthetic resin comprising any one or a plurality of: polyethylene, polypropylene, polyurethane, acrylonitrile-butadiene-styrene resin, silicone rubber, and polyurethane rubber which are treated to contain 1-5 wt. % of a natural antibacterial agent; and
    molding the resultant product of the above steps into nanoparticles.

2. The manufacturing method of the nanoparticle composition with antibacterial and exothermic properties of claim 1, wherein the cationic surfactant used has a purity of 99%, has 12-20 carbon atoms, and is any one of cetyl trimethylammonium bromide and cetyl trimethylammonium chloride.

3. The manufacturing method of the nanoparticle composition with antibacterial and exothermic properties of claim 1, wherein the synthetic resin is polyethylene which is any one of Linear LDPE, HDPE, and LDPE.

4. The manufacturing method of the nanoparticle composition with antibacterial and exothermic properties of claim 1, wherein the natural antibacterial agent is prepared using one or a mixture of two or more of spearmint extract, essential oil, grapefruit seed extract, phytoncide, evening primrose extract, juniper leaf extract, bamboo leaf extract, pine leaf extract, tree of heaven leaf extract, ginkgo leaf extract, *salvia* extract, cranesbill extract, and a solution of violacein diluted to 1% concentration in ethanol.

5. The manufacturing method of the nanoparticle composition with antibacterial and exothermic properties of claim 1, wherein the ionized calcium powder preparing stage is composed of a shell injecting process; a foreign substance removing process; a cleaning process; a drying process; a sintering process; a cooling process for quenching the rough shell passed through the sintering process to room temperature; and a pulverizing process for pulverizing the particle size into the size of 3-8 μm, and
    wherein the foreign substance removing process and the cleaning process are performed three times in succession, the cleaning process uses an ultrasonic cleaning method using frequencies above the audible frequency, and the cleaning is performed using alkaline water of pH 8.5-9.0, wherein the sintering process uses a cylindrical sintering furnace having a downward inclination, rotating by a driving device and maintaining a high temperature, and wherein when the purity of calcium is 99% or more, the rotational speed of the sintering furnace is 30 to 35 rpm, the amount of shell is 300 kg/hr, and the sintering temperature is 1,200° C. or more, it is made by keeping the shells in the sintering furnace for 45 to 90 minutes.

6. The manufacturing method of the nanoparticle composition with antibacterial and exothermic properties of claim 5, wherein the alkaline water is prepared by passing underground water through a filter which is made by filling a powder of cockles into a mesh with micropores.

7. The manufacturing method of the nanoparticle composition with antibacterial and exothermic properties of claim 5, wherein said pulverizing process includes a process of coating a surface of ground powder of shells in a spraying manner with a composition formed by containing 0.1 wt. % to 1 wt. % of yellow dye and filling with the cationic surfactant as the remainder.

8. A nanoparticle composition prepared by the manufacturing method of claim 1, mixed into one of paint, wood, or fabric.

9. A nanoparticle composition prepared by the manufacturing method of claim 1, coating any one of a garment, fabric, wood, a glove, or lunch box.

* * * * *